(12) United States Patent
Oberndorfer et al.

(10) Patent No.: US 8,710,848 B2
(45) Date of Patent: Apr. 29, 2014

(54) SENSOR SYSTEM

(75) Inventors: Christian Oberndorfer, Schwäbisch Hall (DE); Katrin Rudolph, Ingelfingen (DE); Michael Winkler, Weissbach (DE)

(73) Assignee: Büerkert Werke GmbH, Ingelfingen (DE)

( * ) Notice: Subject to any disclaimer, the term of this patent is extended or adjusted under 35 U.S.C. 154(b) by 499 days.

(21) Appl. No.: 13/055,393

(22) PCT Filed: Jul. 21, 2009

(86) PCT No.: PCT/EP2009/005285
§ 371 (c)(1),
(2), (4) Date: Apr. 8, 2011

(87) PCT Pub. No.: WO2010/009863
PCT Pub. Date: Jan. 28, 2010

(65) Prior Publication Data
US 2011/0309841 A1 Dec. 22, 2011

(30) Foreign Application Priority Data
Jul. 23, 2008 (DE) .................... 20 2008 009 938 U

(51) Int. Cl.
G01N 27/28 (2006.01)
G01N 27/416 (2006.01)
G01N 27/02 (2006.01)

(52) U.S. Cl.
USPC ........................... 324/450; 324/438; 324/439

(58) Field of Classification Search
USPC ........................ 324/450, 438, 439
See application file for complete search history.

(56) References Cited

U.S. PATENT DOCUMENTS

| | | | |
|---|---|---|---|
| 5,478,526 | A | 12/1995 | Sakai et al. |
| 5,520,787 | A | 5/1996 | Hanagan et al. |
| 5,755,953 | A | 5/1998 | Henning et al. |
| 6,117,290 | A | 9/2000 | Say et al. |
| 6,123,820 | A | 9/2000 | Bergkuist et al. |
| 6,432,720 | B2 | 8/2002 | Chow |
| 6,896,793 | B2 | 5/2005 | Erdosy et al. |
| 2005/0014134 | A1 | 1/2005 | West et al. |
| 2008/0264788 | A1 | 10/2008 | Uthemann et al. |
| 2009/0321258 | A1 | 12/2009 | Abel et al. |

FOREIGN PATENT DOCUMENTS

| | | |
|---|---|---|
| DE | 4310607 A1 | 10/1993 |
| DE | 19747875 A1 | 5/1999 |
| DE | 10353938 A1 | 6/2005 |
| EP | 0450202 A1 | 10/1991 |
| EP | 0189316 B1 | 3/1993 |
| EP | 1371974 A1 | 12/2003 |
| EP | 1710567 A1 | 10/2006 |
| WO | 9419683 A1 | 9/1994 |
| WO | 2008052758 A1 | 5/2008 |

Primary Examiner — Amy He
(74) Attorney, Agent, or Firm — The Webb Law Firm

(57) ABSTRACT

A modular sensor system for continuous measurement of analytes in continuous flow has a fluidic module, a sensor module, an optional reference module, and a cover part which are stacked on top of each other and firmly connected with each other so as to be releasable. The fluidic module includes a fluid duct having an inlet and an outlet. The sensor module includes a sensor compartment which has at least one sensor and is in fluid communication with the fluid duct of the fluidic module. The optional reference module is in fluid communication with the fluid duct of the fluidic module by means of a diaphragm. The cover part seals the sensor module or the reference module.

6 Claims, 6 Drawing Sheets

SENSOR SYSTEM

BACKGROUND OF THE INVENTION

Field of the Invention

The present invention relates to a multi-purpose sensor system which allows continuous measurements of analytes in continuous flow.

SUMMARY OF THE INVENTION

In the sensor system according to the invention which is indicated in the claims, a variety of sensor elements may be utilized, such as, for example, an ISFET for pH determination, a noble metal electrode for redox potential measurements, or polymer diaphragms for ion concentration measurements.

The system is also suitable for physical and electroanalytical measurements.

Advantageously, the sensor system is structured modularly and in layers from plate-type individual parts, the individual layers being adapted to be connected with each other in a sealing, but releasable manner and being exchangeable in a simple way if required.

A fluidic module, a sensor module, an optional reference module, and a cover part are stacked on top of each other as individual layers.

Disposed on the inside of the fluidic module is a flute-like fluid duct having an inlet and an outlet through the plate to an outside, and a duct interruption as a lead-through to the subsequent layer, i.e. the sensor module.

With the exception of the small area of the duct interruption, the bottom of the sensor module layer constitutes a cover for the fluid duct. The duct continues there into a special duct contour through the bottom leading to the sensor compartment; this duct contour serves to achieve an optimum flow against the sensor, which is preferably perpendicular to the sensor, as a result of which any possible undesirable concentration polarization of the sensor is avoided or at least greatly reduced. In this way, accuracy of measurement and reliability are increased.

The sensor module serves as a receptacle for a sensor and further sensors such as a temperature sensor, for example.

When the next layer, i.e. the reference module, is placed on the sensor compartment, the latter is sealed by the bottom thereof.

A reference module together with a diaphragm container forms a reference electrode.

The reference module serves as a container of the electrolyte, preferably a gel electrolyte, required in electrochemical measuring processes. Agar-agar has turned out to be favorable, which contains the electrolyte matching the electrode (for example, 3 M potassium chloride solution for an Ag/AgCl electrode). In order to obtain as long a diffusion path as possible, the container provided for the gel electrolyte may have a meander-shaped design.

A small, for example cylindrical vessel that is open towards the reference module and is likewise filled with an electrolyte can be fitted into a recess in the bottom of the container of the reference module, the vessel being guided in a borehole through the sensor module and protruding as far as to the fluid duct of the fluidic module. A disk-shaped diaphragm is placed into this vessel. A fluidic contact between the reference module and the analyte in the fluid duct is established through an opening in the bottom of the cylindrical vessel, i.e. the reference electrode.

A reference wire such as Ag/AgCl protrudes from outside into the container of the reference module.

The reference module is sealingly closed with a cover.

All the layers are provided with recesses for connection and evaluation electronics.

The modular structure of the sensor system allows it to be easily taken apart into its individual components at any time.

In this way, the fluid duct, which after removal of the sensor module lies openly on the surface of the fluidic module, can be easily cleaned.

Above all when the fluid duct is of a small diameter, there is the risk of the fluid duct becoming clogged by particles present in the analyte or by precipitates that settle out upon reaction with reagents that are additionally metered in the course of the analysis. In systems in which the fluid duct is not accessible, a clogging of the duct could make the whole measuring system unserviceable.

In the sensor module, the sensor element can be simply exchanged, cleaned or replaced, where required.

An aged or defective reference electrode may, depending on the damage, be regenerated by exchanging the diaphragm in the diaphragm container or by removal and refilling of the gel component.

Also, the reference module can be easily cleaned, repaired, or completely exchanged. It is also possible to replace the electrode wire.

Owing to the compact and space-saving design, the system described here is suitable both as a separate device for carrying out various types of ion concentration measurements, depending on the sensor element used, and also as a part of a versatile analysis system in combination with other partial measuring systems which can be used for continuous and parallel or successive acquisition of further physical data such as the degree of turbidity.

In a slightly modified form, the modular sensor system is also suitable for non-electrochemical measuring methods in which no reference electrode is required. Here, the reference module and the diaphragm container are dispensed with, and the respective boreholes for attachment or lead-through are sealingly closed. The sensor module receives the desired sensor such as, for example, a pressure sensor in the sensor compartment and is directly sealed with the closing cover.

DETAILED DESCRIPTION OF THE PREFERRED EMBODIMENT

Figure 1:
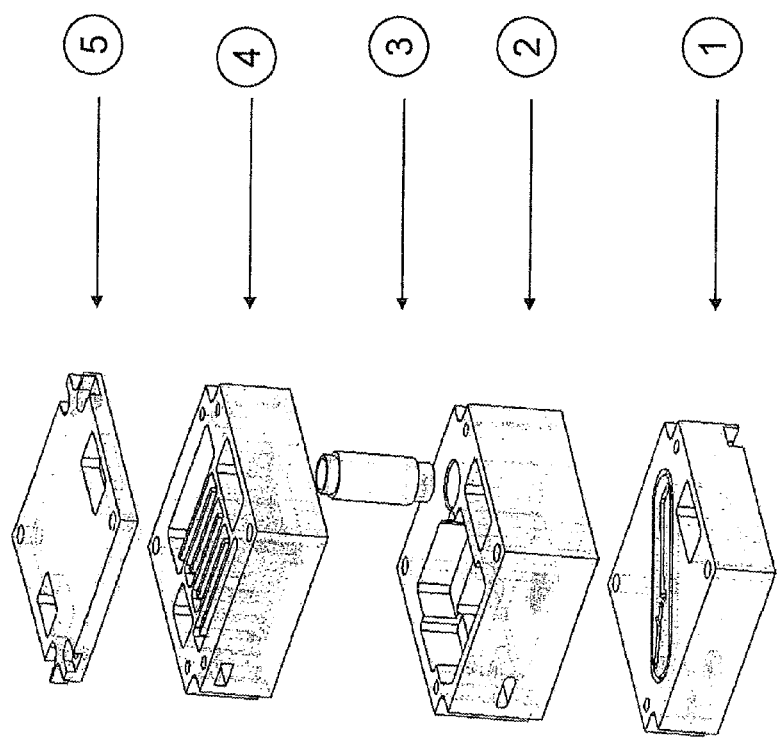
FIG. 1 shows an exploded view of an ion-sensitive measuring system according to the present invention.

As shown in FIG. 1, an electrochemical sensor system is structured modularly and in layers from plate-like, substantially parallelepipedal individual components, namely a fluidic module 1, the sensor module 2, the reference module 4 with an associated diaphragm container 3, and a cover 5.

These individual components are stacked on top of each other and connected with each other firmly but releasably at sites 6 provided therefor. For series production, the individual components can be produced from a plastic material in an injection molding process. But a manufacturing by machining is also possible. A preferred material employed is a chemically resistant plastic material since it is to be avoided in the analysis process that the medium to be determined carries over any additional ions into the measuring process by undesirable reactions with the substrate.

Figure 2:
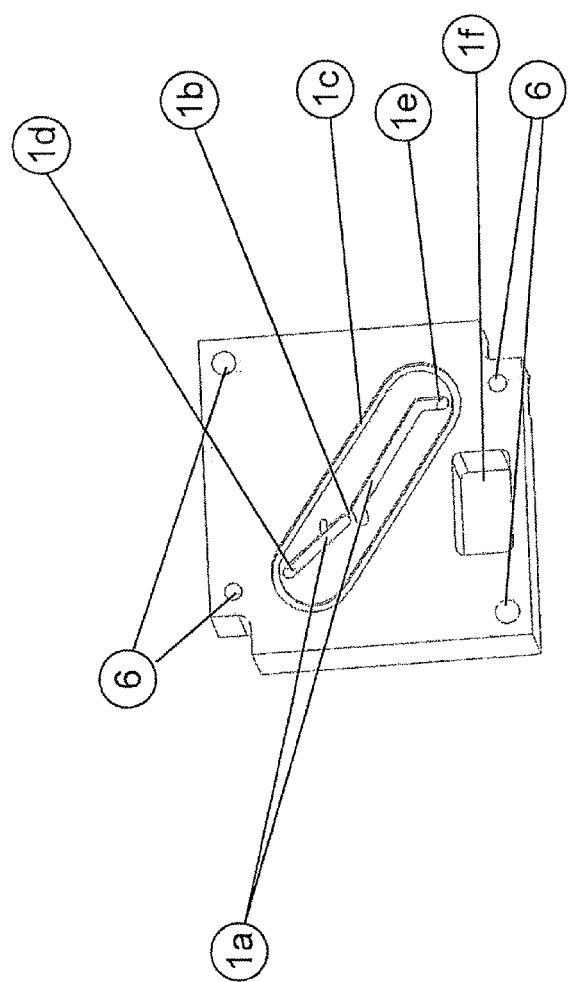
FIG. 2 shows a fluidic module.

Arranged on the side of the fluidic module 1 facing the next following layer is a fluid duct 1a. The fluid duct 1a leads to outer surfaces of the fluidic module 1 by means of an inlet 1d and an outlet 1e. In the exemplary embodiment illustrated in FIG. 2, the flute-like fluid duct 1a extends substantially diagonally on the inside of the fluidic module 1 and is surrounded by the contour 1c that serves to receive a seal.

A recess 1f offers space for a connection electronics required for the measurement.

Depending on the space required by the electronic unit, the recess 1f is continued in the subsequent plates.

Figure 3:
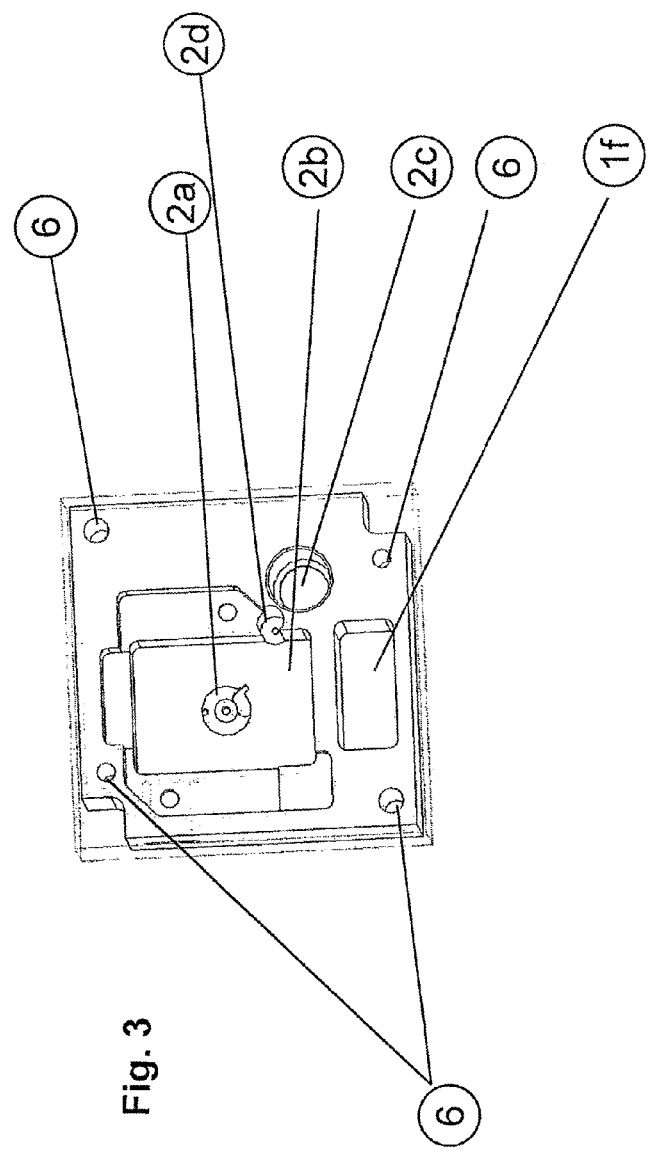
FIG. 3 shows a sensor module.

A duct interruption 1b for lead-through of the analyte provides a fluidic connection to the contour 2a in the bottom of the sensor compartment 2b, which is a part of the next following layer, i.e. the sensor module 2, which is illustrated in FIG. 3.

Depending on the measuring method desired, the appropriate sensor—for example an ISFET for pH measurement—may be placed into the sensor compartment 2b. Here, the sensitive side of the sensor is directed towards the duct contour 2a, which is configured in such a way that an optimum flow against the sensor is attained. Preferably, the flow is perpendicular to the sensor.

The boreholes 2d and 2c are provided for receiving a further sensor, for example a temperature sensor, or for lead-through of the diaphragm container 3.

Figure 4:
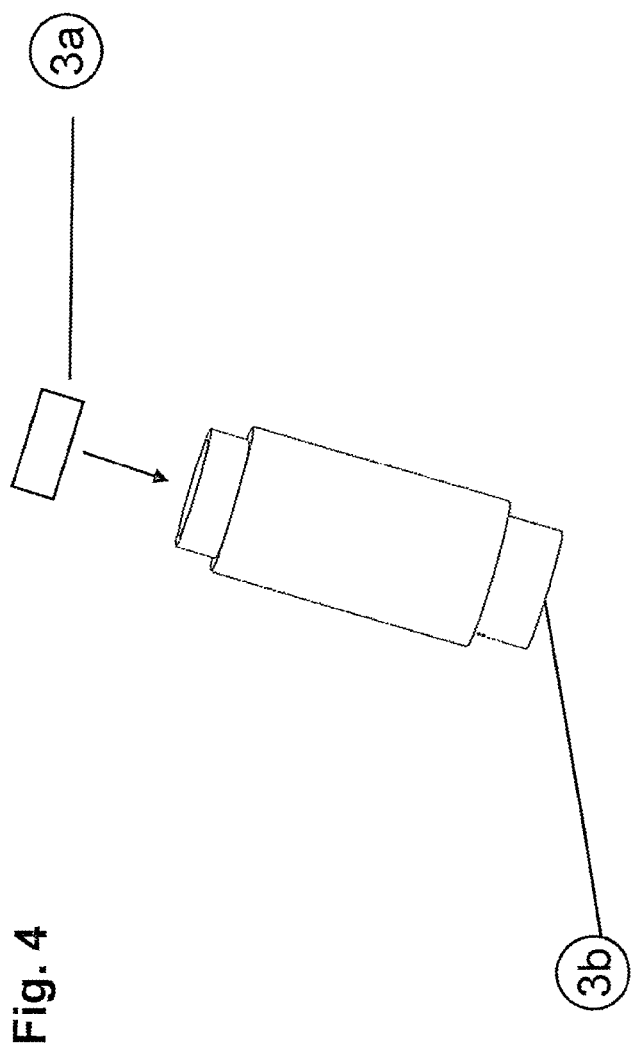
FIG. 4 shows a diaphragm container.

FIG. 4 illustrates the diaphragm container 3. The diaphragm container 3 is constituted by a vessel that consists of a bottom and a jacket and is open on the side opposite the bottom. There is a small opening 3b in the bottom of the diaphragm container 3 as a fluidic connection between the fluid duct 1a and the reference module 4. Arranged inside the diaphragm container 3 above the small opening 3b is a diaphragm 3a.

It consists of a porous material, e.g., glass, ceramics or plastic and, in operation, ensures a fluidic contact between the reference electrode and the fluid in the fluid duct 1a. The diaphragm 3a is permeable, but serves as a filter for any other, solid constituents.

Figure 5:
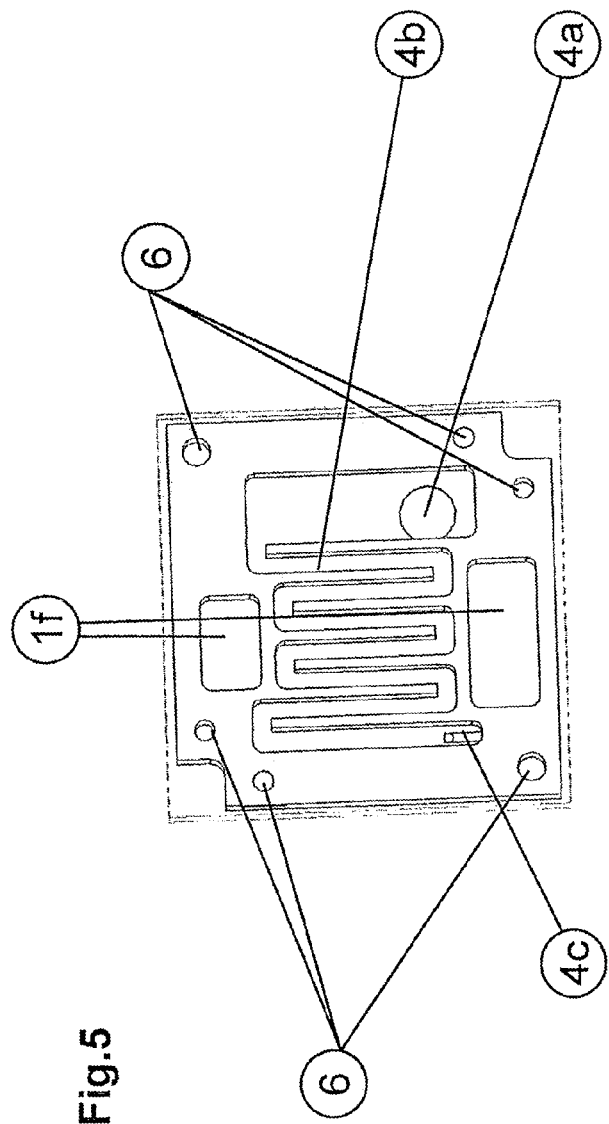
FIG. 5 shows a reference module.

The diaphragm container 3 is fitted by its open end into the insertion opening 4a of the reference module 4, illustrated in FIG. 5. When the reference module 4 is placed on the sensor module 2, the bottom of the diaphragm container 3 moves through the borehole 2c as far as to the fluid duct 1a of the fluidic module 1. At the same time, the sensor compartment 2b is covered and closed by means of the bottom of the reference module 4.

The reference module 4 essentially constitutes a container 4b for the electrolyte required for the measurement. The diaphragm container 3 is likewise filled with electrolyte.

Preferably, a gel electrolyte is used which contains agar-agar as a substrate. Agar-agar has the advantage that it is water-soluble and solidifies.

The container 4b can be of a meander-shaped configuration. This has the advantage of a long diffusion path. The reference electrode is thereby protected against penetration of medium from the fluid duct 1a.

An electrode wire 4c is immersed in the container 4b and is guided through the reference module 4 to an outside.

Figure 6:
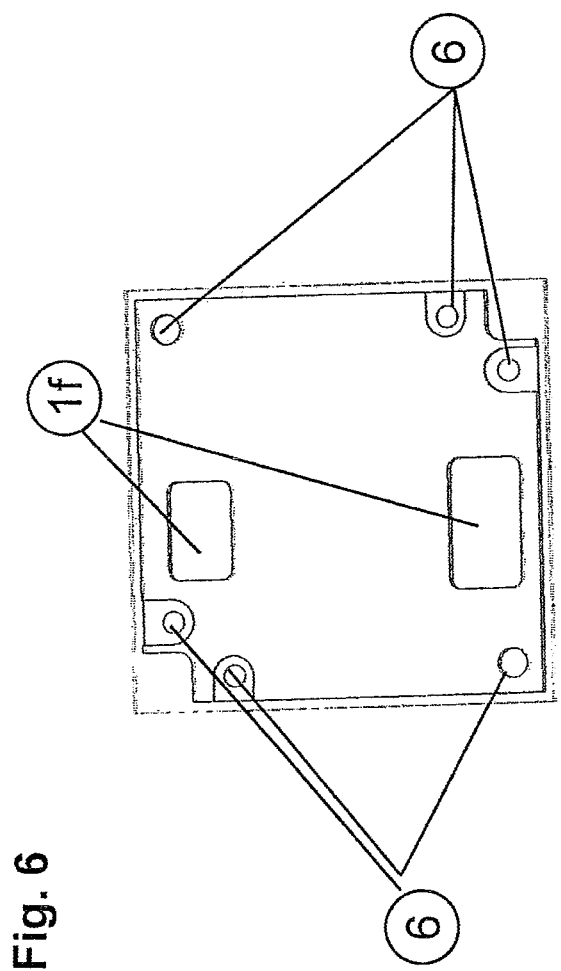
FIG. 6 shows a cover.

The cover 5, which is illustrated in FIG. 6, is placed in a closing manner onto the reference module 4. Provided in the cover 5 are sites 6 for fastening means as well as lead-throughs 1f for connection and evaluation electronics.

The medium to be analyzed moves from the inlet 1d into the fluid duct 1a and to the duct interruption for lead-through 1b. The medium is subsequently received by the contour 2a for the flow against the sensor, contacts the sensor in the sensor compartment 2b, flows via the duct interruption for lead-through 1b back into the fluid duct 1a and continues to the outlet 1e.

If it is intended to apply a non-electrochemical measuring method for determining further physical properties of a fluid, the reference electrode consisting of the reference module 4 and the diaphragm container 3 is dispensed with in the above-described structure of the sensor system.

The fluidic module 1, the sensor module 2 and the cover 5 are stacked on top of each other to form the sensor system, with boreholes for attachment or lead-through of the diaphragm container 3 being sealingly closed for this application. The sensor compartment 2b is then fitted with a pressure sensor, for example.

The invention claimed is:

1. A modular sensor system for continuous measurement of analytes in continuous flow, said system comprising a fluidic module, a sensor module, an optional reference module, and a cover part, which are stacked on top of each other and firmly connected with each other so as to be releasable, wherein
said fluidic module includes a fluid duct having an inlet and an outlet,
said sensor module includes a sensor compartment having at least one sensor and being in fluid communication with said fluid duct of said fluidic module,
said optional reference module is in fluid communication with said fluid duct of said fluidic module by means of a diaphragm,
said cover part seals one of said sensor module and said reference module, and
wherein said reference module includes an electrolyte container which is connected with said fluid duct of said fluidic module by means of a diaphragm container protruding through said sensor module.

2. The sensor system according to claim 1, wherein said sensor compartment is sealed on a side of said sensor module facing away from said fluidic module by one of a bottom wall of said adjacent reference module and said cover part.

3. The sensor system according to claim 1, wherein said diaphragm container forms a vessel that is filled with an electrolyte and is open towards said electrolyte container of said reference module and includes a bottom wall on which a diaphragm rests and which is provided with a borehole that opens into said fluid duct of said fluidic module.

4. The sensor system according to claim 1, wherein said electrolyte container of said reference module forms a meander-shaped duct.

5. The sensor system according to claim 1, wherein an electrode wire projecting into said electrolyte container of said reference module from outside is provided.

6. The sensor system according to claim 1, wherein said modules are provided with aligned recesses for connection and evaluation electronics.

* * * * *